United States Patent [19]
Frenkel et al.

[11] Patent Number: 5,409,828
[45] Date of Patent: Apr. 25, 1995

[54] METHOD FOR STIMULATING CELL MULTIPLICATION, DIFFERENTIATION, EMBROYOGENESIS AND RESPIRATION IN PLANT CELL TISSUE CULTURE BY THE ADDITION OF A GLYCOPROTEIN EXTENSIN TO CULTURE MEDIUM

[75] Inventors: Chaim Frenkel, North Brunswick; Chee-Kok Chin, Spotswood; Daphna Havkin-Frenkel, North Brunswick, all of N.J.

[73] Assignee: Rutgers, The State University of New Jersey, New Brunswick, N.J.

[21] Appl. No.: 538,396

[22] Filed: Jun. 14, 1990

Related U.S. Application Data

[63] Continuation-in-part of Ser. No. 323,061, Mar. 10, 1989, abandoned, which is a continuation of Ser. No. 810,518, Dec. 18, 1985, abandoned.

[51] Int. Cl.$^6$ .......................... C12N 5/00; C12N 5/04
[52] U.S. Cl. ......................... 435/240.4; 435/240.46; 435/240.54
[58] Field of Search .......... 435/240.4, 240.46, 240.49, 435/240.54

[56] References Cited

U.S. PATENT DOCUMENTS 4,801,545  1/1989  Stuart et al. .................... 435/240.49

OTHER PUBLICATIONS

Chen et al. (1985) The Embo Journal, vol. 4, No. 9, pp. 2145–2151.
Osima et al. (1978) *Fronties of Plant Tissue Culture*, Ed. Thorpe, pp. 265–275.
Gamborg et al. (1981) *Plant Tissue Culture*, Ed. Thorpe, p. 26.

*Primary Examiner*—Gary Benzion
*Attorney, Agent, or Firm*—Leroy G. Sinn

[57] ABSTRACT

The invention provides a process for stimulating the multiplication, differentiation or somatic embryogenesis of higher plant cells in tissue culture by the addition to the culture medium an effective amount of extensin preparation derived from higher plant tissue. Also, provided are tissue cultures which have such stimulating amount of extensin present. Finally, provided by the invention is the sterile extensin preparation which has the stimulating activity, preferably the extensin used being pure or substantially pure.

5 Claims, 10 Drawing Sheets

METHOD FOR STIMULATING CELL MULTIPLICATION, DIFFERENTIATION, EMBRYOGENESIS AND RESPIRATION IN PLANT CELL TISSUE CULTURE BY THE ADDITION OF A GLYCOPROTEIN EXTENSIN TO CULTURE MEDIUM

CROSS-REFERENCE TO RELATED APPLICATIONS

This application is a continuation-in-part of U.S. application Ser. No. 07/323,061, filed Mar. 10, 1989, which is a continuing application of U.S. application Ser. No. 06/810,518, filed Dec. 18, 1985, both abandoned.

TECHNICAL FIELD

This invention relates to a higher-plant tissue culture process by which an increase in cell multiplication and differentiation and somatic embryogenesis are obtained in an artificial tissue culture medium by use therein of an effective amount of the glycoprotein extensin, higher plant tissue culture medium and compositions which stimulate higher plant tissue culture when added to a higher plant tissue medium in an effective amount wherein the essential active factor thereof is the glycoprotein extensin.

BACKGROUND ART

Plant cells or explants are grown on artificial media using a method generally known as tissue culture. By this process cells derived from plants are grown in vitro, i.e., in an artificial medium under controlled conditions. The cells can be grown either in an aqueous suspension or in a suitable gel medium or grown attached to a solid support.

In general, cells of plants and explants have been grown using generally known tissue culture methods. It is desired to culture plant cells or explants in such an artificial medium, and to obtain increased cell multiplication and differentiation and development of plant embryo structures, which are progenitors of whole plants. This process of plant embryo development is called somatic embryogenesis.

In the past, it has been possible to culture explants of many higher plants on an artificial nutrient medium. A cluster of cells develop under appropriate conditions on the surface of the explant. This cluster of cells is called a callus. Cells from the callus can be transferred to a liquid culture medium.

The plant cells can maintain their metabolic processes if proper plant cell culture conditions are maintained. The cells must be provided adequate source of required nutrients and oxygen. One of the suitable plant tissue culture media is referred to as a Murashige-Skoog medium. It is described by T. Murashige and F. Skoog in *Physiol. Plant.* 15:473–497 (1962). The culture can conventionally be maintained in a liquid state with agitation, which can be varied as required. The plant cells must be transferred to fresh culture medium periodically to maintain the vigor and growth of the cells.

Embryogenesis is usually induced by manipulation of the plant growth regulator component or, at times, other components of the culture.

Such tissue culture using many higher plant cells, including cells of many important plants, results in no somatic embryos or a low yield thereof.

It is important to obtain significant somatic embryogenesis in a tissue culture process. Tissue culture is a powerful method for propagating certain elite and engineered genotypes as well as more standard ones. It is also highly useful for screening large numbers of plants for desired genetic variants of those plants. One of the shortcomings in the current state of the art is to obtain in a large number of important higher plants a sufficiently large yield of the embryos on a controlled basis. In the past, there has been some success in obtaining multiplication of cells, but the degree of success has been limited in the differentiation of those multiplied cells necessary to obtain effective yields of desired embryos, which then can mature into full plants.

Therefore, it is important to develop a new higher plant cell tissue culture process by which more effective somatic embryogenesis is provided. It is also important to provide a good yield of embryos in the process.

It would also therefore be important to develop plant tissue cultures which would provide a high degree of cell multiplication and differentiation to result in effective somatic embryogenesis by use of a stimulating material to be incorporated into such desired plant tissue cultures.

It has been found that by cell culture processes that production of certain desired plant metabolites such as shibolin have been realized. Shibolin is a useful compound having medicinal as well as pigment properties. Often such chemical metabolites are produced in large measure during a particular stage of plant development. If the development of the culture can be manipulated under controlled conditions using certain culture procedures, it would be possible to produce large quantities of such chemical metabolites efficiently. This would allow production of chemicals from plants not native to particular growing regions where it is desired to produce the chemicals.

By means of effective plant cell culture processes, it would be an important development to be able to produce effectively identical plants from an individual plant specimen by means of improved tissue culture process and by use of a new tissue culture. It would be further important to obtain such plants in good yield. Such a new process would enable the growth of plants which are much more true to original plant specimen than those obtained by growing plants from seeds of the particular plant specimen.

SUMMARY OF INVENTION

This invention relates to a novel method of producing plants comprising culturing higher plant cells in a tissue culture in which an effective amount of the glycoprotein extensin is present. Higher plant cells can be obtained by culturing a higher plant explant on a synthetic nutrient medium. From the plant cell growth or callus that develops on the explant, an amount of cells are removed and dispersed in a nutrient synthetic tissue culture medium.

A conventional general tissue culture procedure can be used for culturing the cells. For example, the cells can be cultured using a liquid medium such as developed by Murashige and Skoog or effective modifications thereof (referred to above and hereafter referred to as "MS"). If the medium is such a liquid medium, the growing cells are maintained in suspension as by moderately rigorous agitation. Aliquots of the dispersed cells are taken and aseptically transferred to fresh volumes of the medium. When desired, the appropriate amounts of plant regulators are added to the tissue culture medium to augment multiplication and differentiation of the cells and to promote somatic embryogenesis.

To the medium is added an embryogenesis stimulating amount of the glycoprotein extensin. Extensin can be derived from higher plant tissue. The tissue is homogenized by using suitable devices and the solid portion containing extensin is isolated and purified as by thorough rinsing with a suitable distilled water, using sterile processing techniques. The extensin can be isolated in pure form by following procedures hereinafter illustratively described in Example 4.

The invention also relates to the sterile purified extensin preparation and also to pure or substantially pure extensin as isolated from said purified extensin preparations and sterile compositions thereof, which are capable of stimulating the multiplication and differentiation of the cells and inducement of embryogenesis of the higher plant cells in the tissue culture medium.

Higher plant cells are selected which are susceptible to such stimulation by adding to the tissue culture an effective amount of extensin.

Finally, the invention also relates to the tissue culture having an effective amount of extensin present by which stimulation of cell multiplication and differentiation and somatic embryogenesis are realized.

The quantity of purified extensin preparation effective will be variable. In general the amount can vary widely and still be effective. For example, an effective amount can usually vary within the range of from about 0.05 to about 50 grams per 100 milliliters of medium, assuming the medium is a liquid culture medium (weights given herein are on a "fresh weight" basis, the sterile extensin preparation customarily having approximately 80 percent by weight of water). Using pure or substantially pure extensin, the corresponding adequate amount added to 100 ml of medium has been ordinarily found to be an effective amount up to about 10 mg.

The process can be carried out using either a solid support system, a suspension system or a gel medium system. However, presently preferred is the suspension system, assuming that the plant cells will multiply and differentiate and that somatic embryogenesis will occur in a suspension system.

Generally speaking, an effective amount of pure or substantially pure extensin has been found to be from about 0.1 mg to about 10 mg, suitably from about 0.3 mg to about 5 mg, usually about 0.3 to about 1 mg being effective.

BRIEF DESCRIPTION OF THE DRAWINGS

FIG. 1 is a photomicrograph of an asparagus cell suspension in MS medium. The magnification is 60×. The cells appear small in size. The presence of organelles (organ bodies appearing in higher plant cells such as chloroplasts-chlorophyll bodies, and the like) in the cells do not appear visible in the figure. No extensin has been added to the tissue culture.

FIG. 6a is a photomicrograph of a cauliflower tissue culture using a standard MS medium. The cells have irregular shape. Organelles are barely visible. The cells have an absence of internal structures and apparently have degenerated and died. The culture has no added extensin preparation. The magnification is 150×.

DETAILED DESCRIPTION OF THE INVENTION

As stated above, the preferred culture technique for carrying out the invention is a suspension cell technique. A suitable medium for use in carrying out the process of this invention can be any appropriate nutrient medium that provides the necessary nutrients and other ingredients for the multiplication and differentiation of higher plant cells and the inducement of somatic embryogenesis. An example of a suitable suspension medium is the MS medium, described generally in the above cited reference. However, sometimes it is preferable, depending upon the plant, to use a gel medium made, for example, using a suitable alginate or other suitable material to provide a solid or semi-solid medium or to use a solid support system such as known in the art.

An effective amount of a sterile extensin preparation is added to the tissue culture medium. Depending upon the economics of a particular cell culture process and the desired amount of stimulation, the amount of sterile extensin preparation used will vary. Also, the optimum amount of sterile extensin preparation for any particular tissue culture will vary. Generally speaking, an amount in the range of about 0.05 to about 50 grams of the sterile extensin preparation as described herein per 100 milliliter quantity of medium is sufficient to provide the desired stimulation. If more highly purified extensin is used, correspondingly lesser amounts on a weight basis can be used. The amount will depend somewhat on the concentration or quantity of the plant cells in the culture. Conventional quantities of plant cells in a tissue culture will respond to an effective amount of the sterile extensin preparation. The most effective and efficient amounts of the sterile extensin preparation to be used in any particular tissue culture should be determined. Too high an amount can cause undesired reactions and will entail a needless cost for extensin. It has been found that an amount of the sterile extensin preparation used is desirably from about 0.5 to about 35 grams per 100 ml of medium, preferably from about 1 to about 20 grams per 100 ml of medium, and from about 1 to about 5 grams per 100 ml of medium being adequate in many tissue cultures to give excellent stimulation based on the herein described extensin preparation. As noted above, weights of the sterile extensin preparation are based upon the "fresh weight" of the preparation, i.e., the weight of the preparation after the free water used in purification is removed as by filtration. The water held by the preparation is removed as by lyophilization, vacuum, drying agents or the like. It is believed that the water content of the sterile extensin preparation, after free water is removed as by filtration, is about 70 to about 85 percent of the total weight. The preparation can be further dried to remove this water insofar as it does not substantially diminish or destroy the stimulating activity of the preparation.

The purified extensin material is prepared using portions of higher plants. In the case of asparagus, for example, the extensin-containing material can be derived from the spears. In the case of cauliflower, the cauliflower curd, which is the flower portion of the cauliflower, can be used. The plant tissues are sterilized prior to preparing the extensin preparation. The sterilization can be carried out by utilization of appropriate commercial household aqueous solutions of sodium hypochlorite, such as sold commercially under the trademark Chlorox. Chlorox product has 5.25 percent by weight content of sodium hypochlorite. The sterilization can also be carried out as by dipping the tissue in ethanol and flaming the surface of the excised material to remove the surface organisms. Other appropriate sterilization means can be utilized which are compatible with the extensin material and effect sterilization.

The making of the sterile extensin preparation is desirably carried out entirely under sterile conditions. All equipment used, all solutions and ingredients used must be sterile. The preparation is suitably carried out in a hood, appropriately a laminar flow hood. The sterilization if appropriate can be done by suitably autoclaving. In the case of instruments used, they are sterilized by autoclaving or can be treated with a high alcohol content solution, such as a 70 percent alcoholic solution.

The sterilized plant material then can be placed into an aqueous solution, for example, an appropriate buffer solution. It has been found suitable to use a potassium phosphate buffer such as a potassium phosphate buffer having a pH of about 7.4. The pH can be adjusted somewhat higher or lower and still be satisfactory. A suitable concentration of the buffer can be selected from about 0.05 to about 1 molar, preferably about 0.1 molar. Other buffers can be used as desired which are compatible with the vitality of the extensin-containing material being processed and the activity thereof in stimulating multiplication and differentiation of the plant cells and the stimulation of somatic embryogenesis in tissue cultures. The amount of the aqueous solution, preferably buffered, used is suitably about 1.5 to 5 times the weight of the sterile extensin-containing material used. It has been found that about one hundred parts of sterile extensin-containing material to 200 parts by weight of buffer is an appropriate combination. It has been found that the processing can be carried out satisfactorily at ambient room temperature.

It is desirable to include a suitable amount of polyvinylpyrolidone or other agent to remove certain components from the plant material, such as phenolic substances. It has been found adequate to use about 1 to about 3 percent of polyvinylpyrolidone, about 2 percent by weight based on the weight of aqueous buffer being adequate.

The mixture of the aqueous buffer and sterile plant material is homogenized using known homogenizing equipment. Suitably the mixture is homogenized using a food processor for a suitable length of time. It has been found that 1 to 5 minutes, suitably about 2 minutes, is adequate in most instances. The homogenate is further homogenized with a high speed homogenizer such as a Virtis homogenizer for a like period, usually about 2 minutes being adequate. The homogenate is then filtered through a suitable sterile filter, such as a filter sold under the designation Miracloth. Other suitable filters can be used. The filtrate is discarded. The solid cell wall preparation is thoroughly washed using double distilled deionized water. It has been found that 15-20 liters of this distilled water is generally a suitable volume for washing of the cell wall material obtained from 100 grams of starting plant tissue.

The washed sterile extensin preparation can be packaged in a suitable container such as in aluminum foil and stored. Storage can suitably be under cold conditions, desirably around $-20°$ C. The thus obtained preparation can be subjected to isolation procedures including hydrolysis, extraction, filtration, etc. such as described in detail in Example 4 hereof.

It will be suggested to those skilled in the art from the above description to make certain modifications to the procedure for preparing the sterile extensin preparation, such as use of different buffers or solvent combinations and additives in forming the homogenates. The sterile extensin preparations so obtained which stimulate the multiplication, differentiation and somatic embryogenesis of higher plant cells in tissue culture are intended to be within the spirit of the invention defined herein.

The medium can also be in gel form, such as made using an alginate. The plant cells can also be attached to a solid medium. These media must be sterile and provide adequate oxygen and nutrients to the cells to sustain their vitality and to permit the functioning of the sterile extensin preparation to be effective in stimulating cell multiplication and differentiation and embryogenesis.

The tissue culture contains effective amounts of indicated plant regulators. Customary plant regulators include 2,4-dichlorophenoxy acetic acid (2,4-D); 6-benzyl amino-purine (BA); indole butyric acid (IBA); indole acetic acid (IAA); naphthalene acetic acid (NAA); kinetin; and at times an effective and compatible amount of others. The selection and amount of plant regulators used will depend in part upon the plant cells grown in the tissue culture.

To the medium also is beneficially added an agent or agents which aid in maintaining sterility of the medium such as anti-bacterial agents and an agent that inhibits multiplication of organisms such as fungi. It has been found useful to use in many tissue cultures the fungistatic agent sold under the trademark Fungizon. Suitable combinations of antibiotic and fungistatic products are available commercially, such as sold by Gibco Laboratories, which contains penicillin base, 10,000 units/ml; FungizonB, 25 mcg/ml; and streptomycin base, 10,000 units/ml. The amount of these agents will be adjusted by those skilled in the art depending upon the medium and plant cells used and other factors.

The receptacles used in the presently preferred aqueous suspension tissue culture system can vary depending upon the scale used. Carrying out the tissue culture at relatively small scale, 125 ml Erlenmeyer flasks adapted for use in tissue culture are satisfactory. Into such a flask is aseptically added an amount of a stock cell culture solution. For example, a 20 ml amount of a stock cell culture has been found to be a suitable amount. Larger or somewhat lesser amounts can be used, and at times will be desirably used.

The cell culture is agitated with a suitable intensity. It has been found that an orbital shaker, when Erlenmeyer flasks are used, is a preferred means of agitating. Other means of causing the desired agitation can be used.

A wide variety of higher plant cells can be used which are susceptible to stimulation of plant cell multiplication and differentiation and of the embryogenesis. For example, monocotyledon plant cells such as asparagus plant cells can be used. Monocotyledon plant cells have been found generally speaking to be difficult to culture and to obtain embryogenesis. Dicotyledon plants can be used such as cauliflower cells, although they have been found generally speaking to be very difficult to culture and to obtain embryogenesis. Various grass plants can be used in carrying out the process of this invention. Conifer and deciduous tree cells, legume plant cells such as soybean plant cells, plant cells of the night shade family, domestic plant cells of the family Cucurbitaceae, Atropa belladonna plant cells, and cells of various other higher plants which are susceptible to stimulation by carrying out the process of this invention, can be used.

The plant cells used in the process and tissue cultures of this invention are obtained by first growing calluses of the desired plant. Segments of a plant are taken, sterilized and grown under sterile conditions using a nutrient medium. To sterilize the plant segments, aqueous sodium hypochlorite solutions, ethanol or other suitable sterilizing agents can be used. In the case of cauliflower, for example, one can start with cauliflower seeds. The seeds can be sterilized by treating the seeds with a suitable aqueous hypochlorite solution. The seeds are then washed several times thoroughly with sterile distilled water. The seeds are germinated under sterile conditions and the seedlings are sterilized suitably with a sterile sodium hypochlorite solution such as a 5 percent solution for a time sufficient to sterilize. A suitable medium is used such as an MS medium to which is added agar, such as about 0.5 to about 1.0 percent, suitably about 0.6 percent. Other nutrients and plant regulators are added as desired. Again, the seedlings are thoroughly washed with sterile distilled water. The cotyledons can be removed and suitably sliced along the midrib. The cotyledon portions are aseptically transferred to a sterile medium in a suitable flask. After several days as necessary, using an ambient room temperature and other appropriate growing conditions, calluses appear. Suitable portions of the callus cell growth are removed, such as 5 to 10 mm. amounts, dispersed in a sterile liquid medium to form a dispersion of cells. This dispersion of cells in a sterile tissue culture medium is used to develop a sterile cell culture stock.

In the case of Atropa belladonna, suitable portions of callus can be generated by starting with sterile root sections.

In the case of asparagus, cross-sectional sterile portions of asparagus spears can be used to generate the necessary calluses.

The following Examples are offered in illustration of the invention and are not meant to be limiting.

Extensin Stimulation of Embryogenesis, Multiplication and Differentiation in Plant Tissue Culture Results are presented showing that sterile extensin preparations derived from intact plants wherein the active factor consists essentially of the glycoprotein extensin can promote embryogenesis, multiplication and differentiation in tissue culture.

| Abbreviations: | |
|---|---|
| cv | Cultivar |
| MS | Murashige & Skoog medium |
| 2,4-D | 2,4-Dichlorophenoxy Acetic Acid |
| BA | 6-Benzyl Amino-purine |
| PVP | polyvinylpyrolidone |
| IBA | Indole Butyric Acid |
| IAA | Indole Acetic Acid |
| NAA | Naphthalene Acetic Acid |

EXAMPLE 1

Culture Systems

1. Asparagus (cv 354-A) cell suspension culture is grown in MS medium amended with 5 micro-molar 2,4-D. Samples are held in 125 ml Erlenmeyer flasks, shaken on a shaker at a rate of 254 rpm, and is sub-cultured every 3 days. The culture is used as stock for later experiments.

In a typical experiment 20 ml aliquots of the stock cell suspension are added to the 20 ml amounts of the amended medium (as above). To the medium aliquots are added sterile cell wall preparation weighing between zero to 10 g fresh weight, as indicated in each experiment.

Freedom from contamination is achieved by using sterile extensin preparation (obtained as described in section B), manipulation of the samples in a sterile hood, and by further supplementation of the culture medium with one ml Fungizon and 1 ml of antibiotic-antimycotic reagent (GIBCO Laboratories) per 100 ml medium. Each flask is examined for contamination by microscopy and plating. Usually the rate of contamination, if any, is low. Contaminated samples are discarded.

The flasks containing the various extensin treatments are placed in 125 ml Erlenmeyer flasks and are held with shaking (as above) for differing time periods. Samples are taken periodically from the flasks for microscopic observations, measurement of respiration and other metabolic parameters as indicated below.

2. Cauliflower Callus

Cauliflower (Brassica oleracea var. botrytis) callus is initiated from seedlings as follows:

a) Aseptic germination is obtained by soaking the seeds twice in undiluted stock sodium hypochlorite solution. First the seeds are washed for 5 minutes in the sodium hypochlorite solution to which is added couple drops of the product Tween 80 as a wetting agent. This treatment is followed by 4 rinses with sterile distilled water.

b) Seeds are germinated on a moist filter paper in a petri plate for 48 hours in dark incubation at 27° KC. The seedlings are then sterilized once more (as described above).

c) Each individual seedling is placed in a 25×100 mm culture tube having 12.5 ml of an MS medium containing 0.6 percent agar, 3 percent sucrose, and 5 ppm ancymidol. The culture is maintained in 18-hr. light intervals at 26° KC. Just prior to the expansion of the first true leaves, cotyledons are excised and cut into two pieces by slicing the cotyledon along the midrib and placing each single piece of tissue on 12.5 ml of an MS medium containing 0.6 percent agar, 3 percent sucrose, 1 micro-molar 2,4-D, and 5 micro-molar BA. After 14–18 days of dark culturing at 27° KC., callus is removed from the cotyledon and cut into 5–10 mm pieces.

Callus (6 g fresh weight) is placed in 20 ml of agar medium containing 2 mM 2,4-D, 2 mM IAA, 2 mM IBA and 5 mM kinetin and the callus-medium mixture is agitated at a rate of 100 rpm. The agar plate callus is used to test the effect of added sterile extensin material.

3. Atropa belladonna Callus, Roots and Embryos

Callus cultures of Atropa belladonna are initiated from seedling roots. Seedlings are obtained from seeds germinated in the greenhouse. Roots are excised from the seedlings, surface sterilized by soaking in 70 percent ethanol for 30 seconds, and then in undiluted sodium hypochlorite bleach for 15 minutes, followed by 4 rinses with sterile distilled water. The media of White (1954), *The Cultivation of Animal and Plant Cells,* Roland Press, N.Y., p. 74, modified by Wood and Braun (1961), "Studies on the regulation of certain biosynthetic systems in normal and crown-gall tumors." (a) (Proc. Nat. Acad. Sci. M.S.A.) (a) b(47): 1907, containing 2 percent sucrose, 0.8 percent agar (Agar-Agar, U.S. Biochemicals, Cleveland, Ohio), 2 mg/l NAA, and 0.5 mg/l kinetin, pH 5.2, is used to initiate callus. The formed callus is subcultured every 4 weeks.

To regenerate roots, 2 grams(fresh weight) of callus is transferred to 125 ml conical shake flasks with 50 ml of medium containing 10 mg/l tropic acid in place of NAA and kinetin. Root regeneration begins several days after transfer. An orbital shaker (New Brunswick Scientific Co., New Brunswick, N.J.) at 280 rpm is used. The roots are harvested after three weeks. The shake culture is used as test material to examine the effect of added sterile extensin material.

EXAMPLE 2

Preparation of Extensin Material

Asparagus spears or cauliflower curd (inflorescence) are used as source of tissue to obtain cell wall material. Field or greenhouse grown plants are used.

Usually 100 g of tissue are homogenized in 200 ml of 0.1M potassium phosphate buffer, pH 7.4, with 2 ml N-octanol as emulsifier, 4 g ascorbic acid and 4 g PVP. Homogenization is carried out for 2 minutes in a food processor followed by additional 2 minutes of high speed homogenization in a VIRTIS homogenizer. The obtained slurry is filtered and rinsed through a MIRA-CLOTH filter (Calbiochem) using 16–20 liters of double distilled deionized water. The homogenization and rinse is repeated.

The entire procedure is carried out under sterile conditions as follows:

1. Prior to homogenization, the asparagus spears and/or the cauliflower curd are dipped in ethanol and flamed to surface sterilize the tissue.
2. All solutions are sterilized by autoclaving.
3. Instruments are sterilized when possible by autoclaving or with 70 percent ethanol solution when necessary.
4. The entire procedure is carried out in a laminar flow hood.
5. The obtained extensin preparations are examined for contamination by plating and when contaminated are discarded.
6. The sterile extensin preparations are stored in (sterile) aluminum foil at −20° KC. until used.
7. The transfer of the sterile purified extensin material to the tissue culture test systems is carried out in a laminar flow hood and according to the microbiological protocol for avoiding center contamination.

EXAMPLE 3

Figure 1:
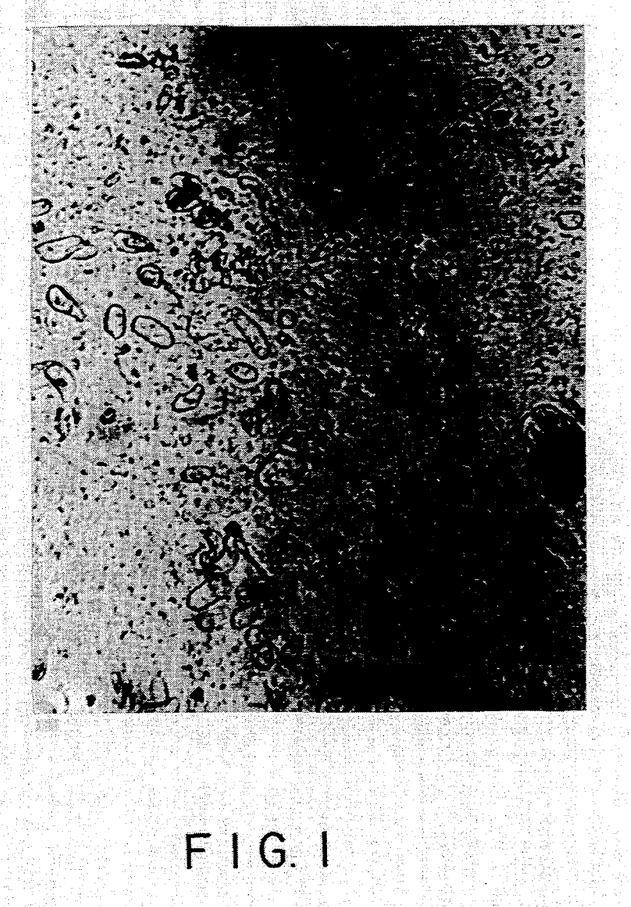

Effect of Added Cell Wall Material on the Growth, Development and the Metabolism of Tissue Culture Systems 1. Microscopic Observations.

a. In the asparagus suspension cell culture in orthodox MS media, and without added extensin preparation, most cells appeared as ghost structures with poorly defined morphology and ultrastructure. There is some evidence of mitotic activity (FIG. 1).

Figure 2:
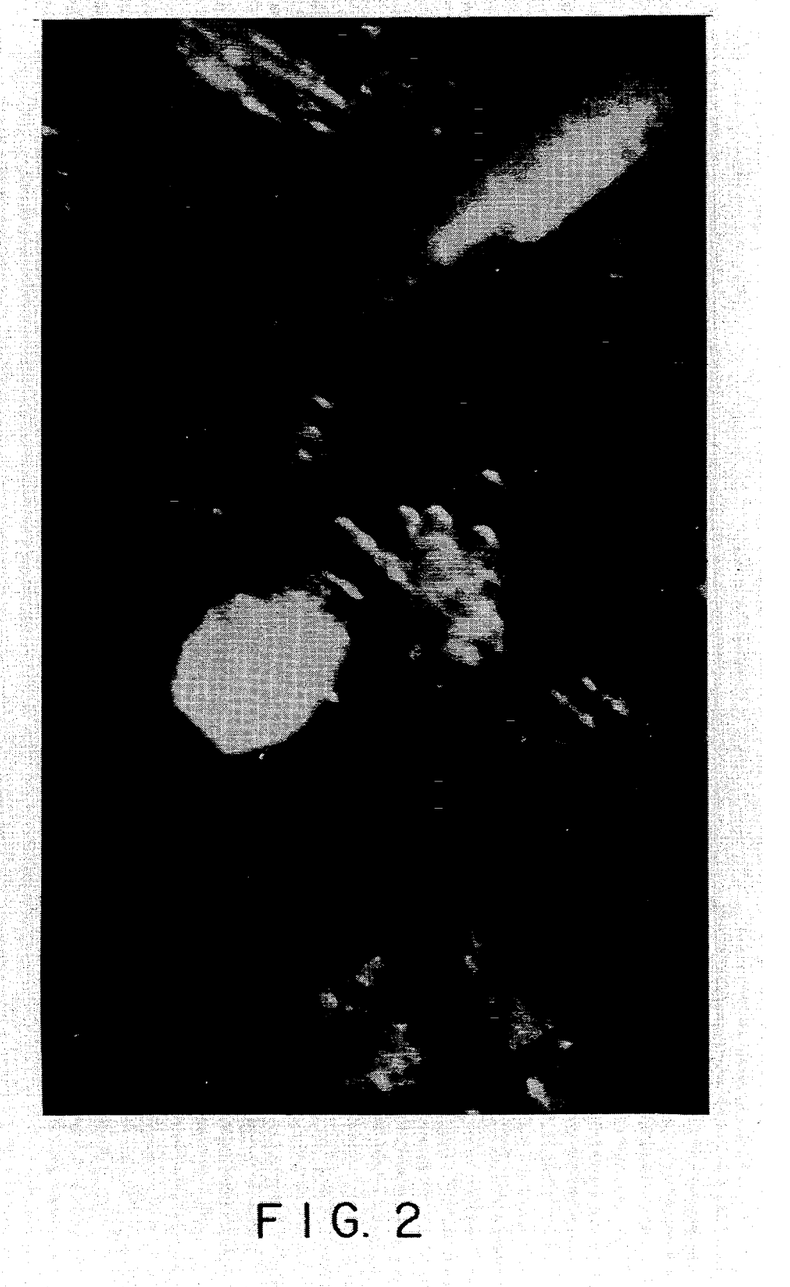
FIG. 2 is a photomicrograph showing a cell aggregate 1 which appears to be in the process of division next to an early embryo structure 2 in asparagus tissue culture having added the extensin preparation. The magnification is 40×.

When the extensin material is added, the following changes are observed:

1) cell aggregates appear apparently a result of mitotic activity (FIG. 2).

Figure 3:
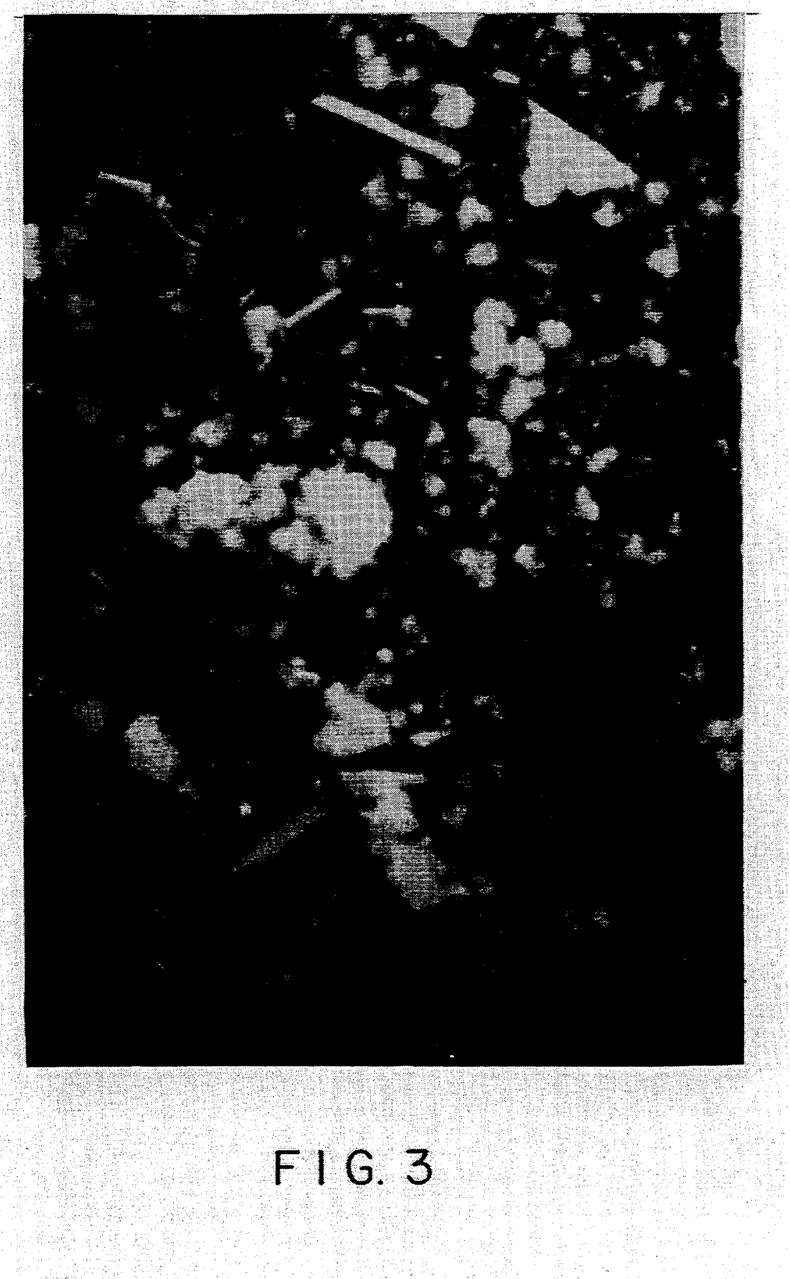
FIG. 3 is a photomicrograph of a massive formation of cell aggregates, apparently in early embryo structures 1 in asparagus tissue culture having added the extensin preparation. Some of the added extensin-containing preparation particles 2 are shown. Magnification is 10×.

2) numerous pre-embryo structures appear ( FIG. 3).

Figure 4:
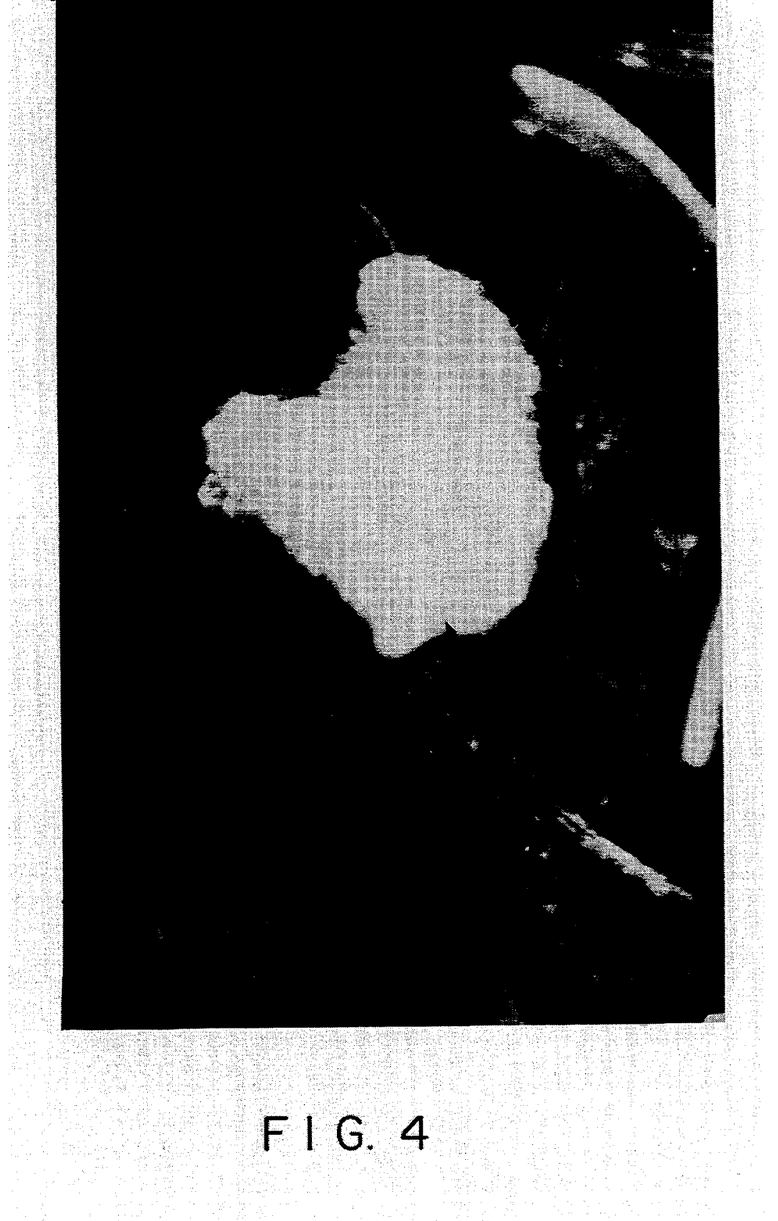
FIG. 4 is a photomicrograph of a torpedo-shaped embryo 1 in asparagus tissue culture having added extensin preparation (some of the added extensin preparation particles 2 are shown). The magnification is 40×.

3) embryogenesis is initiated by the formation of a characteristic torpedo-shaped structure (FIG. 4).

Figure 5:
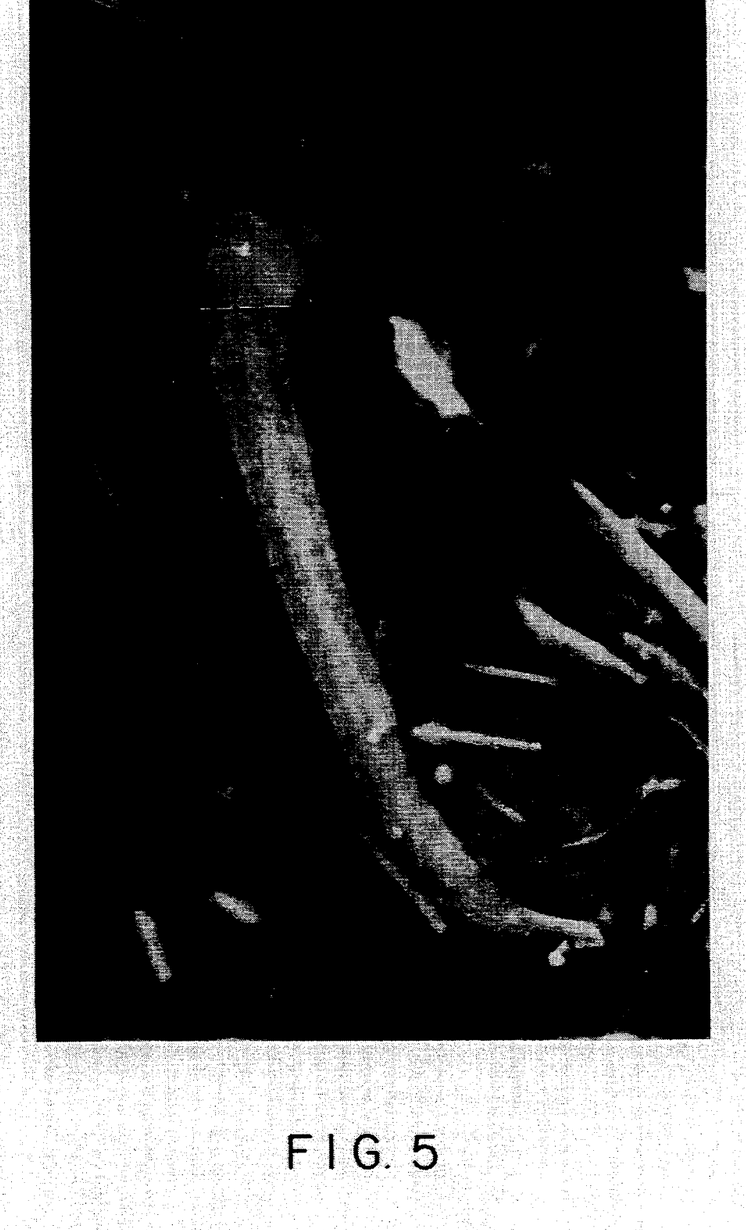
FIG. 5 is a photomicrograph of a progressive stage of embryogenesis showing a well-defined radical 1 and epical meristem 2 in asparagus tissue culture having added extensin preparation. The magnification is 25×. Meristem means the growing cell tip portion of a plant. Radical pertains to a root portion of a plant and epical pertains to apex stem portion.
Figure 6A:
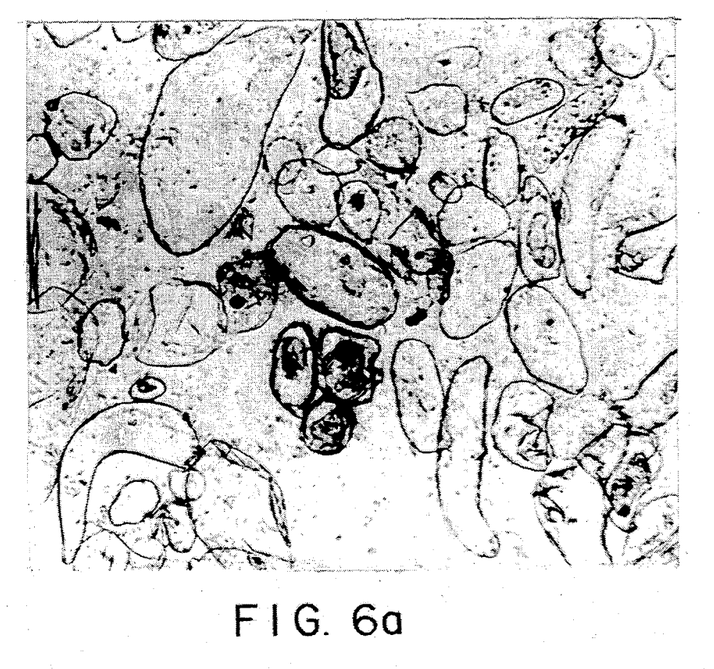
Figure 6B:
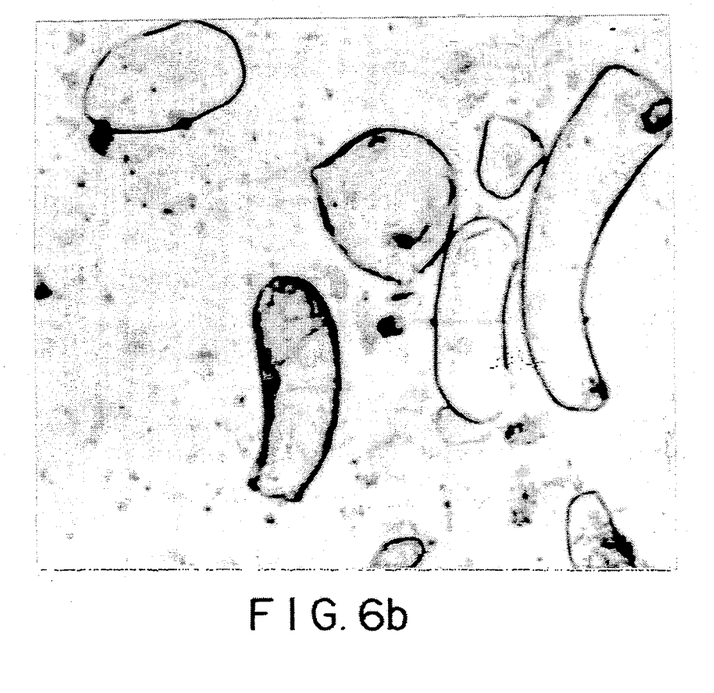
FIG. 6b is an enlargement of a representative cell sample from a photomicrograph of FIG. 6a. The magnification is 300×.

4) developed embryo structures are formed showing well defined radical and epical meristem (FIG. 5).

b. cells of cauliflower tissue cultures normally do not differentiate and display unicyclic generation pattern apparently because mitotic activity is low or absent. In orthodox MS media (FIG. 6) cultured cells appear mostly as ghost structures due to degeneration.

Figure 7A:
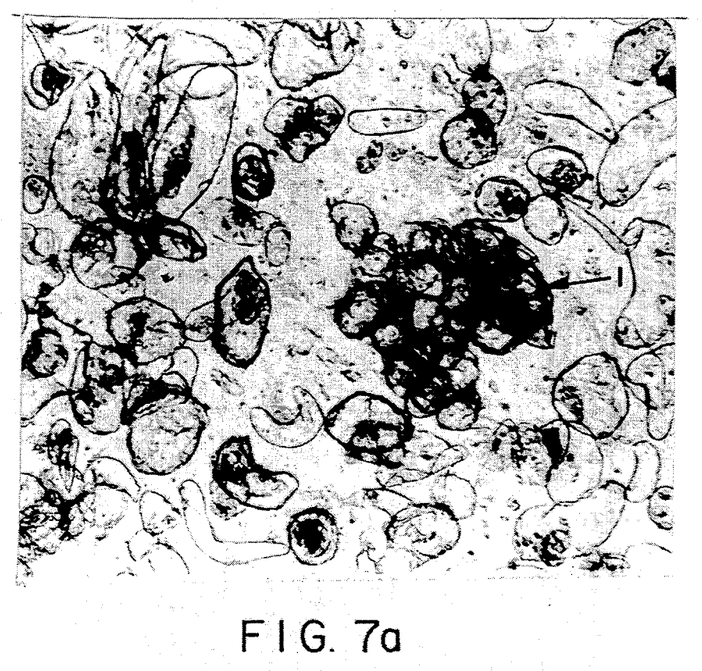
FIG. 7a is a photomicrograph of cauliflower cells from an MS medium tissue culture having added sterile extensin preparation. The photomicrograph clearly shows that the cells have defined organelles, particularly nuclei and that the cells are in the process of aggregation 1. The magnification is 150×.
Figure 7B:
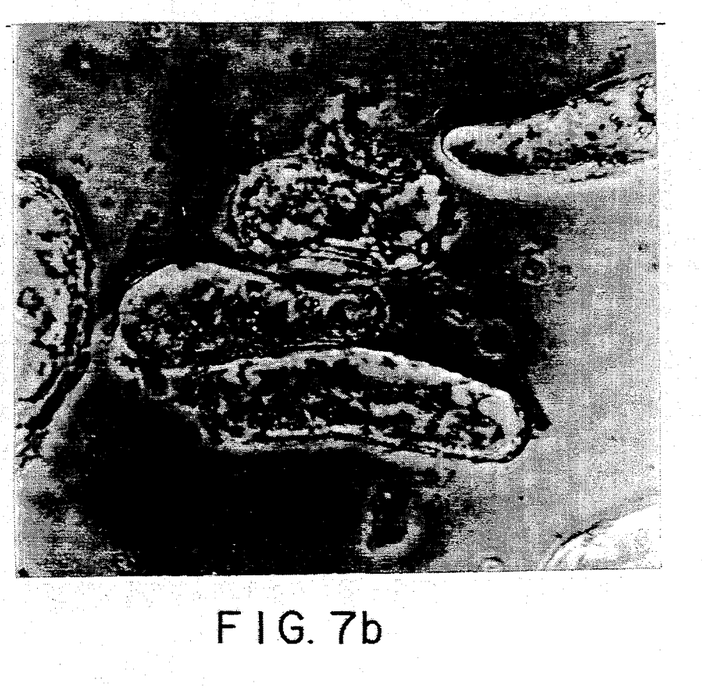
FIG. 7b is an enlargement of an area of the photomicrograph of FIG. 7a using a phase contrast microscope. The cells shown have well-developed internal structures. The enlargement has a 300× magnification.

In the presence of added sterile purified cell wall preparation, cells attain distinct morphology. Well defined organelles including the nucleus and chloroplasts are visible (FIG. 7). There is also evidence for mitotic activity.

c. Atropa belladonna

Figure 8:
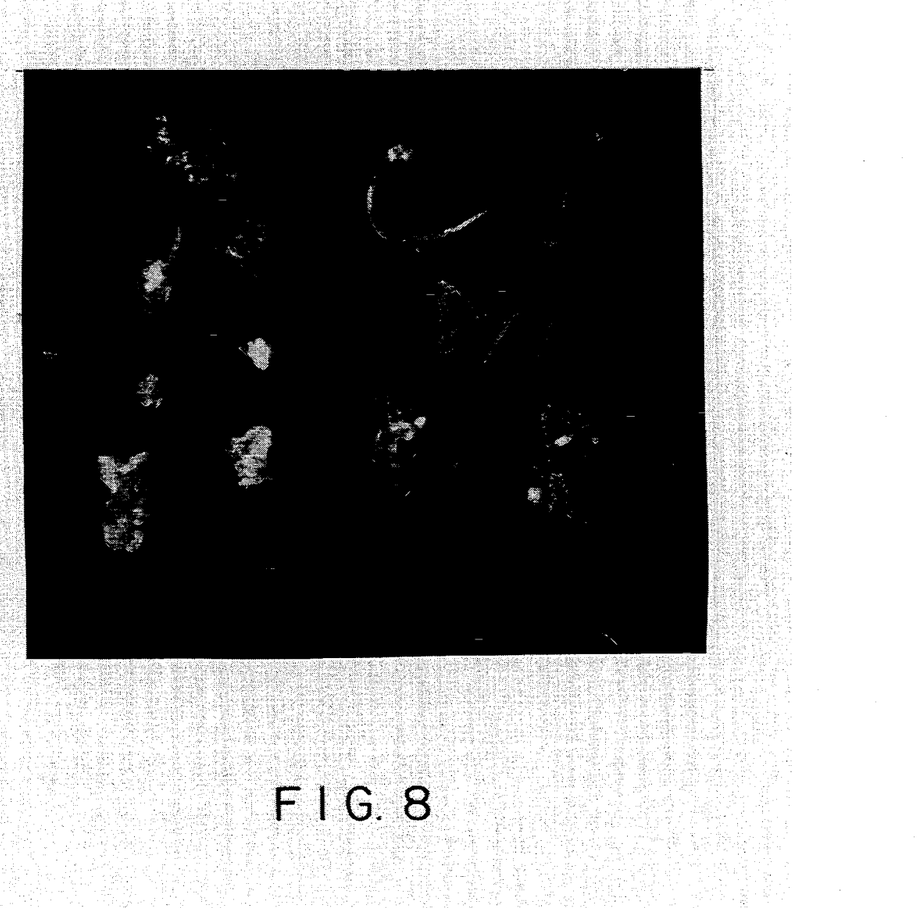
FIG. 8 is a photomicrograph of a Belladonna root callus showing growth response in a standard MS medium with no added sterile extensin preparation (two columns on left) and in contrast with added sterile extensin preparation (two columns on right). As is shown, the presence of sterile extensin preparation stimulates cell differentiation including shoot (epical) and root (radical) organogenesis, and also stimulates somatic embryogenesis on the shoot surface. The magnification is 10×.
Figure 9:
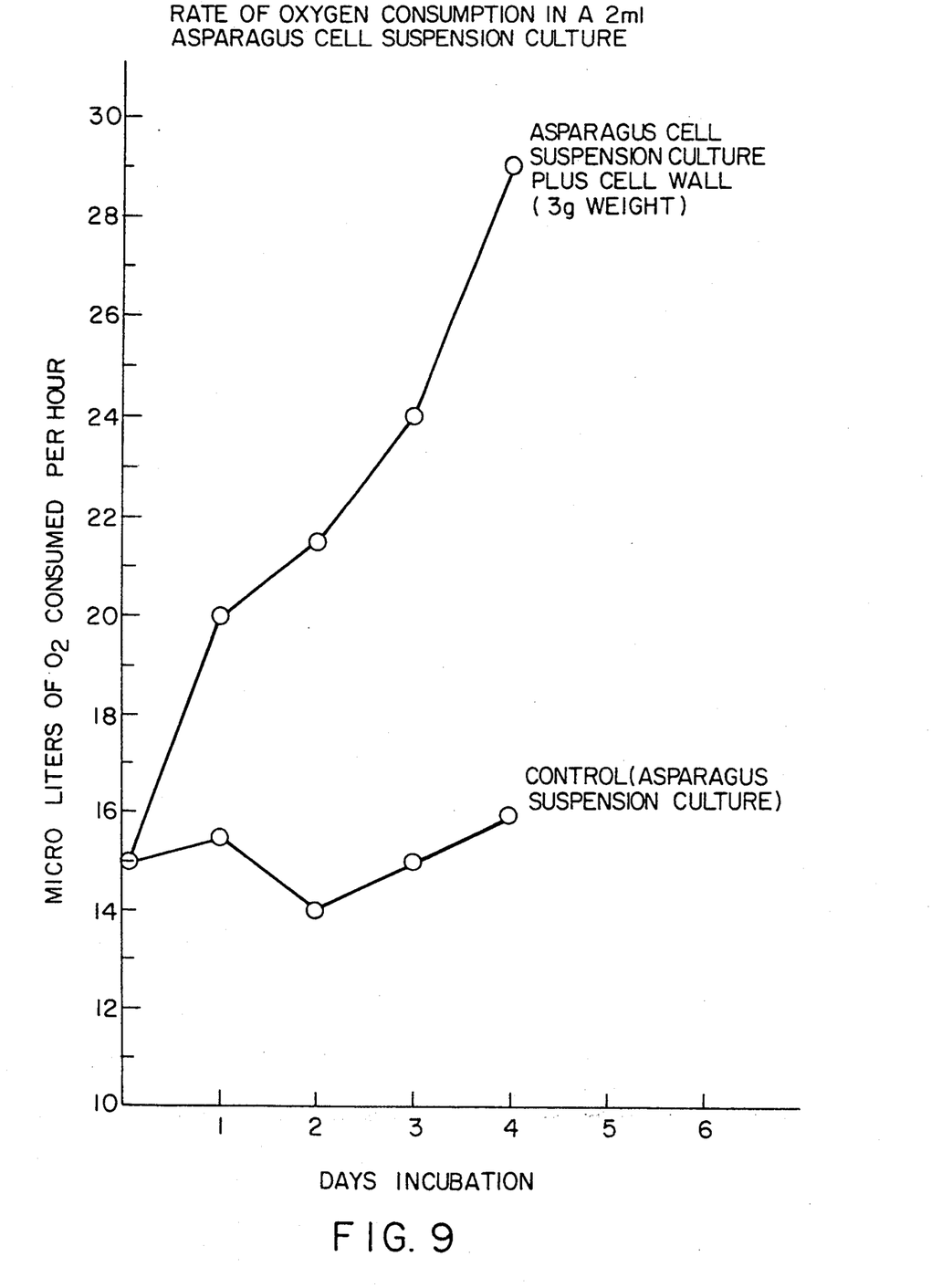
FIG. 9 shows graphs of the respiratory pattern of a culture of asparagus cells in suspension using MS medium having no added sterile extensin preparation and in contrast with added sterile extensin preparation (3 g/40 ml). The graphs show that presence of sterile extensin preparation stimulated respiratory activity.
Figure 10:
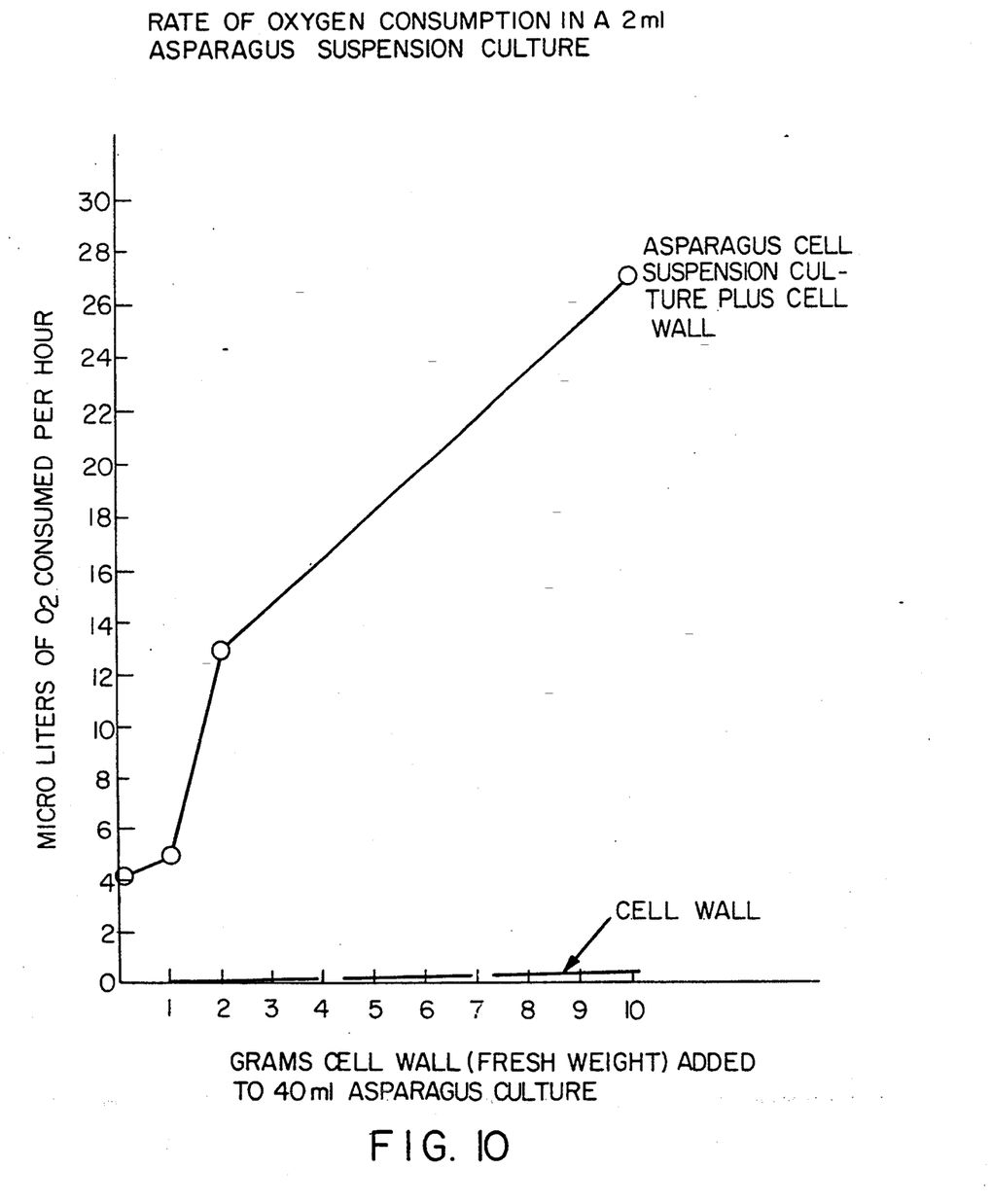
FIG. 10 shows graphs of respiratory activities of a tissue culture having asparagus cells in an MS medium in which differing amounts of sterile extensin preparation are added. The graphs show a dose response for the sterile extensin preparation.

The addition of 1 gram (fresh weight) of freshly prepared autoclaved sterile extensin preparation to shake callus cultures dramatically changes the patterns of the tissue morphogenesis. In a standard culture medium, root organogenesis occurs and is induced by tropic acid. In the presence of tropic acid and sterile extensin preparation, root organogenesis occurs and is followed by shoot organogenesis, and then by the proliferation of numerous adventitive somatic embryos on the surfaces of the shoots (FIG. 8). They sometimes appear to be formed in rows. Root formation begins after several days, shoots appear by about two weeks, and embryos by about three weeks.

2. Growth and Metabolic Activity a. Asparagus cell aggregates are recovered by filtration from cell suspension culture. The collected samples weighing 1.0 g are placed in 10 ml of standard MS medium amended with 5 micro-molar 2,4-D and are incubated with different amounts of cell wall preparations at 28° C. with shaking. After 5 weeks of incubation, cell aggregates are separated by filtration, dried at 60°–80° KC. for 48 hours and weighed. The filtrate is used for pH measurement as an index of metabolic activity. The results are indicated in Table I.

| Treatment (g cell wall preparation added) | Dry wt of Aggregates (mg) | Percent increase | pH (of the filtrate) |
| --- | --- | --- | --- |
| 0 (control) | 30 | — | 5.8 |
| 0.5 | 20 | −33 | 6.6 |
| 1.0 | 75 | +150 | 6.5 |
| 2.0 | 70 | +130 | 6.6 |

The added sterile extensin preparation (above 0.5 g) stimulated the growth of the cell aggregates (roughly doubling in weight).

The pH change is also used as an index of metabolic activity. [A rise in pH indicates a release into the medium of hydroxyl ions, apparently in exchange for the uptake of nitrate ions, and hence an index of metabolic activity.] The observed rise in pH indicating enhanced metabolic activity is commensurate with the increase in the cell wall induced growth. These data are in agreement with the microscopic observation showing enhanced growth and development when extensin preparation is added to the culture medium.

b. Similar effects are obtained in cauliflower callus when cultured with added sterile extensin preparation.

Three grams of callus obtained as outlined above are added to a 125 ml flask containing standard MS medium plus 2 micro-molar IBA, 21 micro-molar IAA and 5 micro-molar kiniten. The samples are supplemented with 0.5 g cell wall preparation, and are incubated at 28° KC. with agitation (95 rpm) for 3–4 weeks. At the end of this period changes in dry weight, pH, and the visual appearance are recorded, as shown in Tables II and III.

TABLE II

Effect of added extensin preparation on the growth rate of cauliflower callus.

| Treatment (g extensin preparation added) | Dry wt of callus (g) | Percent change | pH (in the medium) |
| --- | --- | --- | --- |
| 0 (control) | 0.23 | — | 6.7 |
| 0.5 g | 0.31 | 34.7 | 7.6 |

TABLE III

Growth responses of cauliflower callus[1] with and without added cell wall material.

| Treatment (g extensin added) | Viability[2] | Ghost[3] structures | Cell[4] aggregates |
| --- | --- | --- | --- |
| 0 | 1 | 3 | 1 |
| 0.5 | 3.5 | 1.5 | 2 |

[1]Cells which disassociated from the callus are used for observation.
[2]Viability, based on the appearance of organelles and cytoplasmic streaming is rated on a scale of 0 to 4 (highest).
[3]Appearance of ghost structures is used as a reciprocal measurement of viability and is rated on a scale of 0 to 4 (worst).
[4]Cell aggregation is used as an index for mitotic activity. Aggregation is rated on a scale of 0 to 3 (highest).

The results corresponded to the observations in the asparagus:

The enhanced viability and the progressive disappearance of degeneracy (Table III) suggest that the added sterile extension preparation restored to the culture growth promoting conditions.

There is the indication that in (extensin) treated cultures there is mitotic activity suggested by the increase in the tissue mass (Table II) and cell aggregation (Table III).

3. Respiration

Respiration is measured by the consumption of $O_2$ with an oxygen electrode unit (Hanastech, D. W.). Two ml samples of the culture are placed in the reaction vessel and the rate of $O_2$ decrease in the medium is recorded over 10 minutes. Respiration is defined as changes in oxygen consumer per unit time.

FIG. 1 shows that in asparagus cell culture, without added extensin preparation, there is little or no change in respiratory activity after 4 days of incubation. By comparison, in samples with added cell wall (3 g fresh weight per 40 ml culture) the respiration increased steadily and after 4 days it is roughly 60 percent higher than the control.

When different extensin preparation quantities are added (0 to 10 g fresh weight/40 ml sample) and the cell cultures allowed to incubate for 5 days the respiration increases substantially and is in proportion to the added extensin preparation (FIG. 2).

It is clear that the added extensin preparation stimulated respiratory activity. It is reasonable to assume the respiratory increase may reflect a change in the growth condition of the metabolic activity of the culture. The respiratory changes are commensurate with the results showing an increase in cell mass (FIGS. 2 through 5) and growth and metabolic activity (Table I).

EXAMPLE 4

The orange, edible portion of fresh carrots is used to obtain a sterile extensin preparation. The edible carrot portion is thoroughly homogenized and processed generally by the procedure described in Example 2.

An amount of 1 kg of the fresh sterile extensin-containing preparation obtained is extracted with 4 liters of 0.3M calcium chloride aqueous solution for a period of about 3 hours with use of stirring during the extraction. The extensin preparation slurry is filtered to remove the solid, undissolved material. The filtrate is concentrated using ultrafiltration and a filtration membrane permitting material having a molecular weight of up to about 10,000 to pass through the membrane.

Trichloroacetic acid is added to the filtrate containing the desired product to a concentration of 10 percent. The mixture is permitted to stand overnight. The solid precipitate is removed by centrifugation. The supernatant is dialyzed using a membrane to remove trichloroacetic acid. The material after dialysis is subjected to gel electrophoresis. The separated product shows a positive result in the Coomasie protein test. It is shown to be a glycoprotein defined as extensin. The extensin-containing aqueous solution is filtered using a 0.45 micron filter to remove microorganisms. The extensin is highly soluble in water. The sterile solution of extensin can be stored in the refrigerator for future use to stimulate multiplication, differentiation or somatic embryogenesis of higher plant cells in tissue culture.

The aqueous solution of extensin can also be freeze dried to provide a white powder, shown to be highly pure extensin by gel chromatography, which can be dissolved as a sterile aqueous solution for such stimulation in tissue culture.

The yield obtained of extensin is 30 mg from the original 1 kg of the starting carrot derived extensin-containing preparation.

The extensin preparation obtained provides desired activity to stimulate multiplication, differentiation and somatic embryogenesis at about 0.3 to about 1 mg per 100 ml of tissue culture medium, whereas the starting sterile extensin-containing preparation provides the desired activity at about 1–5 g (1000–5,000 mg) on a dry weight basis per 100 ml of tissue culture medium. The extensin preparation shows in the process and tissue culture of this invention to provide desired multiplication, differentiation or somatic embryogenesis stimulating activity in the range up to about 10 mg/100 ml of tissue culture medium, suitably about 0.1 to about 10 mg/100 ml of tissue culture medium, desirably from about 0.1 to about 5 mg of the extensin preparation/100 ml of tissue culture medium, depending upon the tissue culture medium used including the population of cells therein. It is contemplated that certain modifications of the extensin could further enhance the potency of the extensin preparation.

Extensin from other higher plant tissues can be isolated in like manner.

The data indicates that most or substantially all of the stimulating activity of the sterile extension preparation is recovered in the final extensin preparation.

The above tissue culture experiments are repeated using corresponding amounts of pure or substantially pure extensin for stimulation instead of the sterile extensin preparations used.

What is claimed is:

1. A method of plant cell tissue culture in which a sterile preparation of a glycoprotein extensin is added to cell culture medium in an amount sufficient to effectively stimulate cell multiplication, cell differentiation, somatic embryogenesis and increase in cellular respiration, said extensin is the glycoprotein isolated by the process comprising:
    a) homogenizing 100 grams of fresh *Daucas carota* L. root tissue for 4 minutes in 200 ml of 0.1M potassium phosphate buffer at pH 7.4 with 2 ml of N-octanol as an emulsifier, 4 grams each of ascorbic acid and PVP in which the slurry produced is filtered and rinsed with 16–20 liters of double distilled deionized water, said process is repeated to obtain 1 kg of fresh sterile extension-containing-slurry;
    b) extracting the 1 kg slurry with 4 liters of 0.3M calcium chloride aqueous solution for a period of about 3 hours with stirring during the extraction;
    c) filtering said slurry to remove the solid, undissolved material followed by filtrate concentration using ultrafiltration and a filtration membrane which permits material having a molecular weight of up to 10,000 to pass through the membrane; and
    d) adding trichloroacetic acid to a final concentration of 10% in which the mixture is allowed to stand overnight followed by centrifugation to remove the solid precipitate formed, then dialyzed to remove the trichloroacetic acid, and filtered using a 0.45 micron filter to remove microorganisms to obtain the extensin-containing aqueous solution.

2. The method of claim 1 in which the amount of extensin added to the cell culture media to stimulate cell multiplication, differentiation, somatic embryogenesis and increase in cellular respiration is about 10 mg per 100 ml.

3. The method of claim 1 in which the tissue culture media is a liquid media.

4. The method of claim 3 in which the tissue culture media is a MS-type media.

5. The method of claim 4 wherein dicotyledonous plant cells are cultured.

* * * * *